US012239325B2

(12) United States Patent
Couture et al.

(10) Patent No.: US 12,239,325 B2
(45) Date of Patent: Mar. 4, 2025

(54) INTEGRATED ROBOTIC SURGERY SYSTEM WITH TOURNIQUET SYSTEM

(71) Applicant: ORTHOSOFT ULC, Montreal (CA)

(72) Inventors: Pierre Couture, Montreal (CA); Victor Cerda-Carvajal, Montreal (CA); Andrew Freiberg, Weston, MA (US); Matthew J. Mcdonell, Mason, OH (US)

(73) Assignee: ORTHOSOFT ULC, Montreal (CA)

( * ) Notice: Subject to any disclaimer, the term of this patent is extended or adjusted under 35 U.S.C. 154(b) by 772 days.

(21) Appl. No.: 17/376,398

(22) Filed: Jul. 15, 2021

(65) Prior Publication Data

US 2022/0015770 A1  Jan. 20, 2022

Related U.S. Application Data

(60) Provisional application No. 63/120,323, filed on Dec. 2, 2020, provisional application No. 63/052,137, filed on Jul. 15, 2020.

(51) Int. Cl.
*A61B 17/135* (2006.01)
*A61B 17/00* (2006.01)
*A61B 34/20* (2016.01)
*A61B 34/30* (2016.01)

(52) U.S. Cl.
CPC .......... *A61B 17/1355* (2013.01); *A61B 34/30* (2016.02); *A61B 2017/00057* (2013.01); *A61B 2017/00106* (2013.01); *A61B 2034/2072* (2016.02)

(58) Field of Classification Search
None
See application file for complete search history.

(56) References Cited

U.S. PATENT DOCUMENTS

| 4,204,545 A | * | 5/1980 | Yamakoshi | A61B 5/026 600/502 |
| 5,979,453 A | * | 11/1999 | Savage | A61N 1/403 606/41 |
| 6,358,208 B1 | * | 3/2002 | Lang | A61B 5/412 600/438 |

(Continued)

FOREIGN PATENT DOCUMENTS

CN  111281471 A * 6/2020 ........... A61B 17/135

OTHER PUBLICATIONS

Paolini et al, "Lower extremity arterial inflow is adversely affected in patients with venous disease", 2008, Journal of Vascular Surgery vol. 48 No. 4, pp. 961-962 (Year: 2008).*

*Primary Examiner* — David Earl Ogg
(74) *Attorney, Agent, or Firm* — NORTON ROSE FULBRIGHT CANADA LLP

(57) ABSTRACT

A system for controlling a tourniquet pressure may have a processing unit and a non-transitory computer-readable memory communicatively coupled to the processing unit and comprising computer-readable program instructions executable by the processing unit. The system may obtain ultrasound readings indicative of a blood flow in a limb having a tourniquet applying pressure on the limb; determine characteristic(s) of the blood flow from the ultrasound readings; and adjust a tourniquet pressure as a function of the at least one characteristic of the blood flow. An integrated robotic surgery system is also provided.

20 Claims, 4 Drawing Sheets

(56) References Cited

U.S. PATENT DOCUMENTS

| | | | |
|---|---|---|---|
| 9,662,088 B2 | 5/2017 | Pelissier et al. | |
| 10,410,746 B2 | 9/2019 | Moctezuma de la Barrera et al. | |
| 2006/0253150 A1* | 11/2006 | McEwen .............. | A61B 17/135 606/202 |
| 2016/0249879 A1* | 9/2016 | Mauldin, Jr. ........ | A61B 8/5223 600/437 |
| 2017/0132788 A1* | 5/2017 | Venugopal ............ | G16H 50/30 |
| 2020/0360027 A1* | 11/2020 | Marcus ................ | A61H 9/0092 |
| 2021/0212658 A1* | 7/2021 | McGrath ............... | A61B 34/25 |

* cited by examiner

INTEGRATED ROBOTIC SURGERY SYSTEM WITH TOURNIQUET SYSTEM

CROSS-REFERENCE TO RELATED APPLICATION

The present application claims the priority of U.S. Patent Application No. 63/052,137 filed on Jul. 15, 2020 and of U.S. Patent Application No. 63/120,323, filed on Dec. 2, 2020, both of which are incorporated herein by reference.

TECHNICAL FIELD

The present application relates to computer-assisted surgery systems with robotic devices, and with tourniquet systems.

BACKGROUND OF THE ART

Computer-assisted surgery may encompass a wide range of devices, including surgical navigation, pre-operative planning, and various robotic devices. Typically, in an operating room, floor space is occupied by the operating table, surrounded by medical personnel. With the advent of medical devices and computer-assisted surgery system, operating room floor space may become congested. A maneuvering of medical equipment may thus be required, even intra-operatively, as a response to floor space constraints.

SUMMARY

In accordance with an aspect of the present disclosure, there is provided a system for controlling a tourniquet pressure, comprising: a processing unit; and a non-transitory computer-readable memory communicatively coupled to the processing unit and comprising computer-readable program instructions executable by the processing unit for: obtaining ultrasound readings indicative of a blood flow in a limb having a tourniquet applying pressure on the limb; determining at least one characteristic of the blood flow from the ultrasound readings; and adjusting a tourniquet pressure as a function of the at least one characteristic of the blood flow.

In accordance with another aspect of the present disclosure, there is provided an integrated robotic surgery system comprising: a casing; at least one processor unit; a robotic arm mounted to the casing; a fluid waste management subsystem having at least one reservoir, and a vacuum pump in the casing; a robotic controller module and a waste management module operated by the processor unit; and an interface having a display screen, the display screen producing graphic-user interfaces associated with both the robotic controller module and the waste management module.

DETAILED DESCRIPTION

Figure 1:
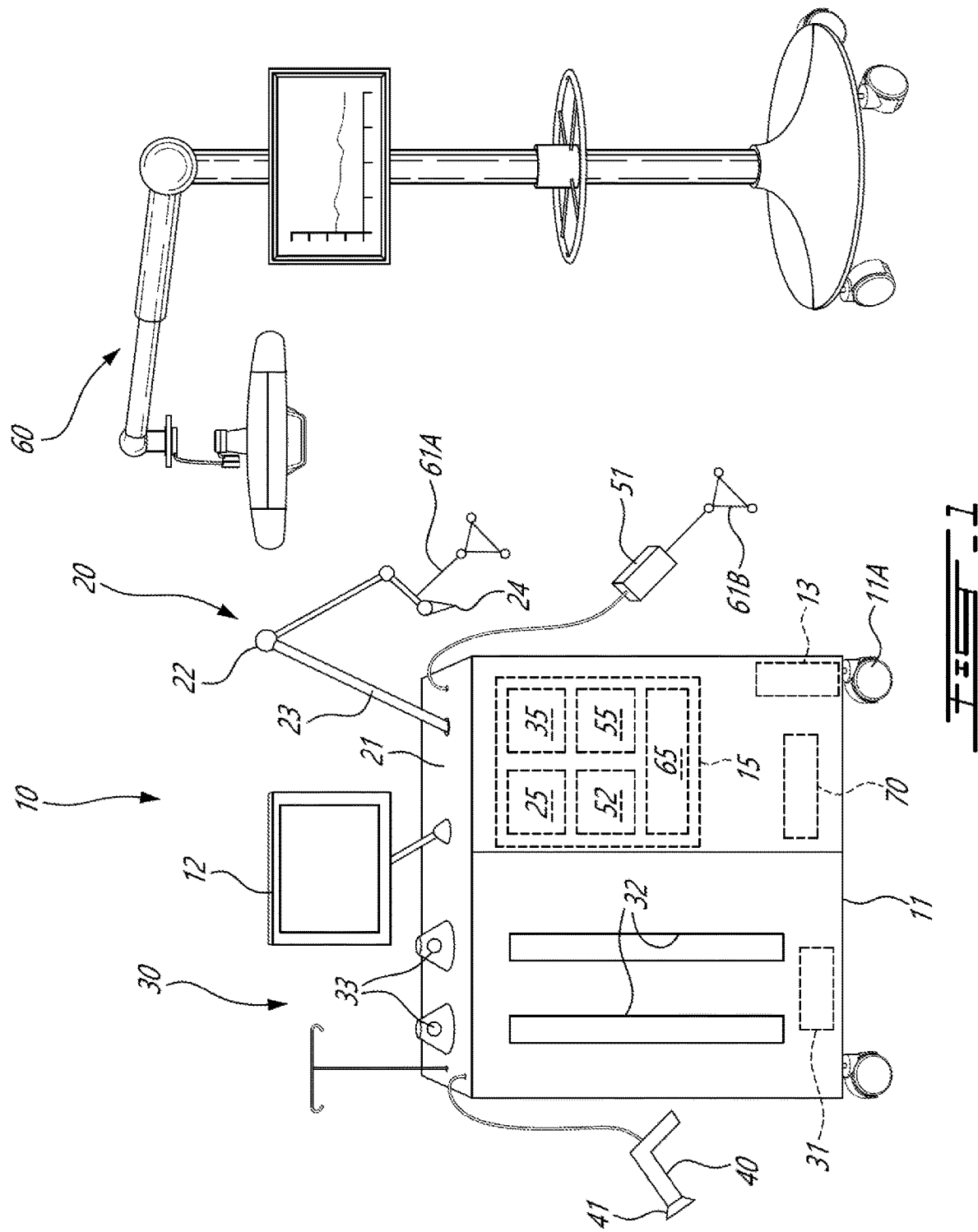
FIG. 1 is a schematic view of integrated robotic surgery system with tourniquet system in accordance with the present disclosure.
Figure 2:
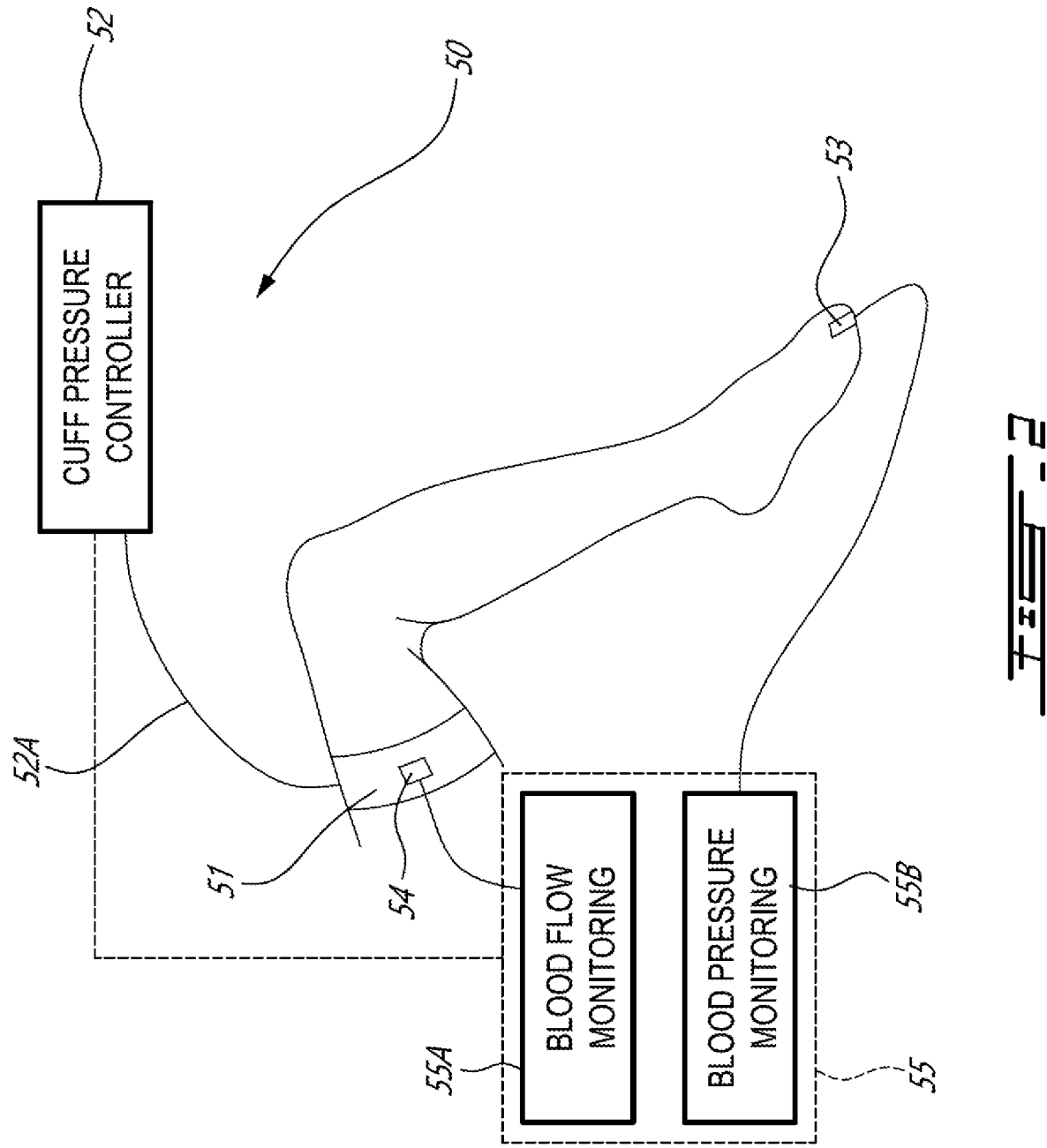
FIG. 2 is a schematic view of a leg with the tourniquet system of the integrated robotic surgery system of FIG. 1.

Referring to the drawings and more particularly to FIG. 1, an integrated robotic system is generally shown at 10, and is used to perform computer-assisted surgery (CAS). A part of the integrated robotic surgery system 10 is shown in FIG. 2 relative to a patient's knee joint in supine decubitus, but only as an example. The system 10 could be used for other body parts, including non-exhaustively hip joint, spine, and shoulder bones.

The integrated robotic surgery system 10 has a casing 11, also known as a base, a station, a platform, a housing, a table, a body, that integrates multiple systems or subsystems described herein below. The casing 11 serves as a base for these multiple systems or subsystems. The casing 11 advantageously reduces the global footprint of numerous apparatuses used jointly during surgery, notably by integrating the multiple systems or subsystems in the single casing 11. For example, the footprint of the casing 11 is less than 8.0 ft$^2$, the footprint being the projection of the casing 11 onto the ground. While some implements may extend beyond the footprint of the casing 11, the implements may be movable in nature (e.g. robot arm) and may thus not be part of the footprint. In an embodiment, the casing 11 may be on casters 11A (wheels, rollers), with or without swivel joints, to facilitate the maneuvering of the casing 11. The casters 11A, if present, may have a lock feature to ensure that the casing 11 remains in a fixed position if desired. As an example, the casters may be as described in U.S. Pat. No. 10,640,136, incorporated herein by reference.

Figure 4:
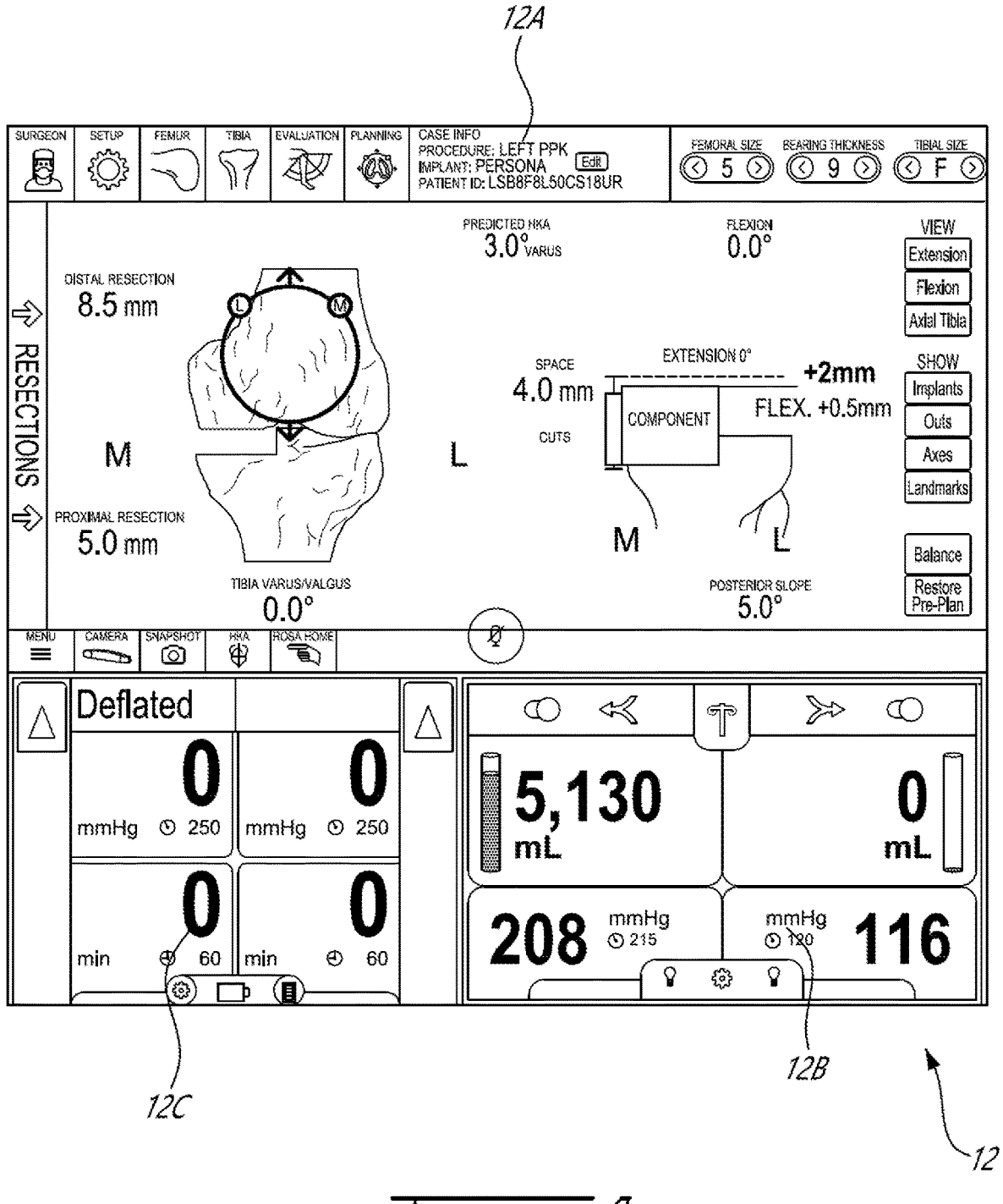
FIG. 4 is a display view of an exemplary graphic-user interface used with the integrated robotic surgery system of FIG. 1.

The integrated robotic surgery system 10 may have one or more interfaces 12, one of which is shown as a screen (e.g., a touchscreen), and mounted to the casing 11 by way of an articulated stand. The integrated robotic surgery system 10 may comprise various types of interfaces 12, for the information to be provided to the operator. The interfaces 12 may be monitors and/or screens including wireless portable devices (e.g., phones, tablets, AR/VR helmet, visor, head-mounted gear), audio guidance, LED displays, among many other possibilities. For example, the interface 12 may include a graphic user interface (GUI) operated by the system 10. In an embodiment, the interface 12 is shared by the multiple systems or subsystems of the integrated robotic surgery system 10, as shown in FIG. 4, with zones 12A, 12B and 12C being exemplary zones associated with the different systems or subsystems. The interface 12 may produce an augmented reality display via projector or augmented reality headset worn by the surgeon or other operating room staff.

Still referring to FIG. 1, the integrated robotic surgery system 10 may have a power module 13, also known as a power bar, power station, etc. The power module 13 may be the single point of connection to a power source for the integrated robotic surgery system 10, with the power module 13 powering the various systems and subsystems of the integrated robotic surgery system 10. Moreover, the power module 13 may include various components to shield the integrated robotic surgery system 10 from power variations, power outages, etc. The power module 13 may for example include a battery. The power module 13, or other parts of the integrated robotic surgery system 10 may connect to an external vacuum source and/or an external compressed air source, like a main facility pneumatic network.

A processor unit 15 may run various modules, in the form of algorithms, code, non-transient executable instructions, etc, in order to operate the various systems and subsystems of the integrated robotic surgery system 10 in the manner described herein. The processor unit 15 may be part of any suitable processor unit, such as a personal computer or computers including laptops and desktops, tablets, server, etc.

The integrated robotic surgery system 10 may be robotized, and has or may have a robot arm 20, a fluid waste management system 30, a debridement system 40, a tourniquet system 50. The robot arm 20, and the systems 30, 40 and 50 may be referred to as subsystems as they are integrated to the integrated robotic surgery system 10. The integrated robotic surgery system 10 may be used with or may further include a tracking system, including a tracking camera 60 as an example thereof.

Still referring to FIG. 1, the robot arm 20 is used to perform various functions associated with the type of surgery of the integrated robotic surgery system 10. For example, the robot arm 20 may be used in orthopedic surgery, and may thus perform bone alterations as planned by an operator. While operable in an automated fashion, the robot arm 20 may also be configured for collaborative/cooperative mode in which the operator may manipulate the robot arm. For example, the tooling end, also known as end effector, may be manipulated by the operator.

Figure 3:
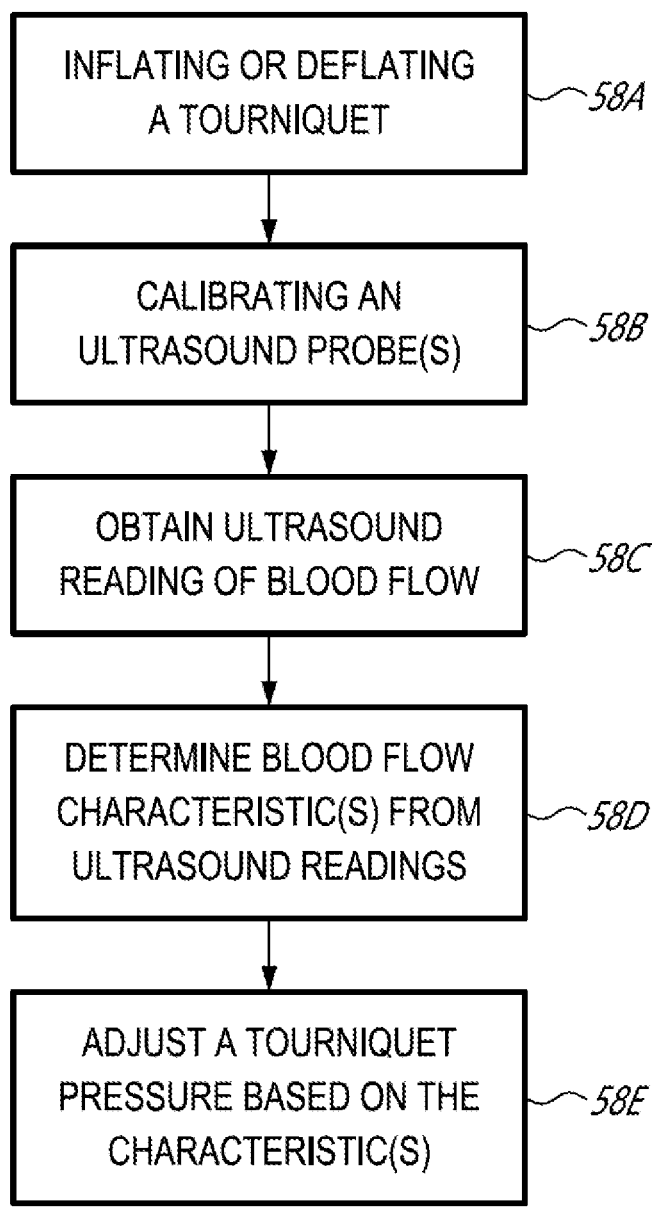
FIG. 3 is a flowchart illustrating a method of adjusting a tourniquet cuff pressure in the tourniquet system of FIG. 2.

The robot arm 20 has a base 21 that is part of the casing 11. The robot arm 20 has a plurality of joints 22 and links 23, of any appropriate form, to support an end effector 24 that interfaces with the patient. For example, the end effector 24 may incorporate a force/torque sensor for collaborative/cooperative control mode, in which an operator manipulates the robot arm 20. The robot arm 20 is shown being a serial mechanism, arranged for the end effector 24 to be displaceable in a desired number of degrees of freedom (DOF). For example, as shown in FIGS. 2 and 3, the robot arm 20 may controls 6-DOF movements of the end effector 24, i.e., X, Y, Z in the coordinate system, and pitch, roll and yaw. Fewer or additional DOFs may be present. For simplicity, only a generic illustration of the joints 22 and links 23 is provided, but more joints of different types may be present to move the end effector 24 in the manner described above.

A few examples of end effectors 24 are provided. The end effector 24 may support a burr used to resurface or drill a bone. The end effectors 24 may also comprise a chuck or like tool interface, typically actuatable in rotation. The end effector 24 may have laminar spreader plates. The laminar spreader plates are used to spread soft tissue apart to expose the operation site. The laminar spreader plates may also be used as pincers, to grasp objects, etc. As a non-exhaustive example, other tools that may be supported by the end effector 24 include a registration pointer, a reamer (e.g., cylindrical, tapered), a reciprocating saw, a retractor, a laser rangefinder or light-emitting device (e.g., the indicator device of U.S. Pat. No. 8,882,777) depending on the nature of the surgery. The various tools may be part of a multi-mandible configuration or may be interchangeable, whether with human assistance, or as an automated process. The installation of a tool in the end effector 24 may then require some calibration in order to track the installed tool in the X, Y, Z coordinate system of the robot arm 20.

The joints 22 are powered for the robot arm 20 to move as controlled by a robot controller module 25 in the available DOFs, and in such a way that the position and orientation of the end effector 24 in the coordinate system may be known, for instance by readings from encoders on the various joints 22. Therefore, the powering of the joints 22 is such that the end effector 24 of the robot arm 20 may execute precise movements, such as moving along a single direction in one translation DOF, or being restricted to moving along a plane, among possibilities. The powering may include braking or blocking the joints 22, though the braking may also be passive. Such robot arm 20 may be for instance as described in U.S. patent application Ser. No. 11/610,728, and incorporated herein by reference. The position and orientation of the end effector 24 may be calculated using solely the encoders on the various joints. The end effector 24 may also be a camera, or a camera may be positioned at the end of the robot arm 20, adjacent to the end effector 24. The camera may contribute to a tracking of the bone and object. For example, the camera on the robot arm 20 may be as described in U.S. patent application Ser. No. 15/902,420, incorporated herein by reference.

A tracking system, featuring tracking camera 60, may be used in conjunction with the integrated robotic surgery system 10 to track the robot arm 20, and bones of the patient. For example, the tracking device may assist in performing the calibration of the patient bones with respect to the robot arm 20, i.e. determining their position and orientation, for subsequent navigation in a coordinate system (also known as frame of reference, global reference system, etc). The tracking device may be of the type involving optical tracking technology, but may also or alternatively perform image acquisition in optical tracking, using for instance structured light, or three-dimensional (3D) camera tracking, also known as range imaging, depth imaging, in contrast to structured light tracking with structured light pattern projection. Other tracking technologies that may be used include GPS locating, wifi tracking, EM tracking, among other possibilities.

The robot controller module 25 controls the robot arm 20 for instance by receiving the tracking data from the encoders of the robot arm 20, or from the tracking device. The robot controller module 25 may also drive the robot arm 20 through a planned surgical procedure. The position and/or orientation is used by the robot controller module 25 to control the robot arm 20.

The robot controller module 25 may be operated by the processor unit 15 to control movement of the robot arm 20. The robot controller module 25 provides computer-assisted surgery guidance to an operator. In an embodiment, the robot controller module 25 provides a display on the interface 12, in the form of a GUI, for a user to control the operation of the robot arm 20, and have access to navigation data. This is shown for example as part of zone 12A of the GUI of the interface 12, in FIG. 4. The robot controller module 25 is tasked with powering or controlling the various joints of the robot arm 20 based on a surgical workflow. The robot controller module 25 may receive data from the robot arm 20 so as to operate same, and this may include joint position/orientation data (e.g., from encoders, position sensors, etc) to determine the position and orientation of the end effector 24. This may also include data from any appropriate force sensors in the robot arm 20 or on other tools associated with the robot arm 20, and/or power consumption or power feed monitoring for the motors of the robot arm 20 (e.g., current/electric potential monitoring), so as to calculate the forces at the end effector 24. The robot controller module 25 may also receive from the tracking device tracking data representative of the position and orientation of the bones and robot arm 20 and affiliated tools in the referential system X,Y,Z. In an embodiment, the data received is raw and may be calculated into position and orientation of the bones and tools using bone models and the tool models (which may include the models of the robot arm 20. The data from the tracking device may be redundant for the robot controller module 25 which may rely on the sensors/encoders of the robot arm 20 to determine the position and orientation of the arm 20 and of their end effector 24. The forces sensors may be provided on the robot arm 20, or on various tools used by the robot arm 20, to provide force feedback related to the interactions of the robot arm 20 with the bones and limb, which force feedback is representative of soft-tissue tensions. The robot controller module 25 may control the robot arm 20 for the latter to receive instructions that cause it to avoid instruments, accessories, or connections associated with the subsystems. For example, in a collaborate/cooperative mode, the robot controller module 25 may protect a vacuum line of a fluid waste management system from disruption by the robot arm 20, as an example.

The robot controller module 25 may perform actions based on the surgical workflow. The surgical workflow may be a module programmed specifically for any given patient, according to the parameters of surgery desired by an operator such as an engineer and/or surgeon. The parameters may include geometry of selected, planned bone cuts, planned cut depths, sequence or workflow of alterations with a sequence of surgical steps and tools, tools used, etc.

Referring to FIG. 1, the integrated robotic surgery system 10 may further include the fluid waste management system 30 integrated into the casing 11. The fluid waste management system 30 may be described as a system for collecting and disposing of medical waste. The fluid waste management system 30 may include one or more vacuum pumps 31, in fluid communication with one or more containers 32, with two shown in FIG. 1. The containers 32 may also be referred to as receivers, reservoirs, etc, and may include removable liner portions received in the casing 11. The containers 32 are depicted by way of windows that may be present to view a level of fluid in the containers 32. Ports 33 are respectively associated with the containers 32. The ports 33 or fewer or more depending for example on the number of containers 32, may receive manifolds so as to interface fluid suction lines to the fluid waste management system 30. Although a single port 33 is schematically shown for each container, each container 32 may have numerous ports, such as a patient port, a vacuum port and a drain port. The patient ports 33 are in fluid communication with a suction line. A vacuum port extends from each of the containers 32 and is in fluid communication with the vacuum pump 31 so that medical waste is collected in the containers 32 through the suction line connected to the patient port 33, by way of the vacuuming performed by the vacuum pump 31. The fluid waste management system 30 may include other features such as filters, flushing pump, solenoid valves, liquid level detectors in communication with the containers 32, smoke evacuators, etc.

In order to operate the fluid waste management system 30, a waste management module 35 is provided, for instance as a part of a module of the processor unit 15. The waste management module 35 is connected to the vacuum pump 31 and to other electronic components of the fluid waste management system 30. For instance, the fluid waste management module 35 receives signals from liquid level detector and operates the vacuum pump 31 accordingly. In an embodiment, the fluid waste management module 35 provides a display on the interface 12, in the form of a GUI, shown in zone 12B of FIG. 4, for a user to control the operation of the fluid waste management system 30. The position of the tubes and suction level may be tracked in relation to the patient, such that the fluid waste management module 35, or other processor module, can warn the user if a tube is placed in an area of the patient anatomy with an inappropriate vacuum level. For example, the fluid waste management module 35 may warn the user if high level suction is about to be activated in the chest cavity of the patient. These features of the fluid waste management system 30 and other features may be present, for instance as described in U.S. Pat. Nos. 7,879,228; 7,892,420; RE44,920; U.S. Pat. Nos. 8,292,857; 8,827,969; 8,449,510; 9,089,629; 7,879,228; 7,892,420, all of which are incorporated herein by reference. Still referring to FIG. 1, the fluid waste management system 30 may be used in conjunction with a debridement device 40. The debridement device 40 is the handheld unit that is used for instance to perform wound vacuum cleaning and/or wound irrigation. The debridement device 40 is connected to the casing 11 via appropriate tubes or hoses, to receive a pressurized fluid, such as water, and to direct waste fluid to the fluid waste management system 30. The fluid may come from a reservoir within the casing 11, or from a source of fluid that complies with sterility standards. The delivery of fluid and the vacuuming of waste may be done via separate and independent tubes to allow concurrent action. In an embodiment, the operation of the debridement device 40 is controlled via the processing unit 15, for instance through the fluid waste management module 35, to enable the various functions of the debridement device 40, or via its own module. For example, the debridement device 40 may have the capacity of performing concurrent irrigation and suction to allow debris and contaminants removal without flooding the field. The debridement device 40 may feature appropriate finger trigger(s) for high or low pressure operation. For example, a cleaning fluid may be at a high pressure for suitable bone cleaning action, with a low pressure setting that may be used for a more gentle lavage. The debridement device 40 may have adjustable settings. The position and activation status of the debridement device 40 may be tracked such that the processor, for instance via the module 35 or other module, may provide guidance to the user on the GUI of areas in the surgical site that have no received proper debridement according to recommended surgical technique.

In an embodiment, the debridement device 40 may have various interchangeable nozzles 41 as a function of the contemplated use. For example, the nozzles 41, also known as tips, may include features enabling actions such as splash shields, fan spray, radial spray, shower spray, brushing, among other features.

Referring concurrently to FIGS. 1 and 2, the integrated robotic surgery system 10 may further include a tourniquet system or subsystem 50. However, the tourniquet system 50 may be independent from the integrated robotic surgery system 10, for instance as a standalone unit. However, for simplicity, the tourniquet system 50 is described below as being part of the integrated robotic surgery system 10. The components described below for the tourniquet system 50 may be housed in the casing 11, or may use the casing 11 as a base, though the casing 11 could be only for the tourniquet system 50. The tourniquet system 50 is used for controlling a penetration of arterial blood into a portion of a patient's limb to facilitate the performance of a surgical procedure. In FIG. 2, there is depicted a tourniquet cuff 51, a.k.a. the cuff 51, encircling a patient thigh, at a location proximal to surgical site, such as the knee. The tourniquet cuff 51 is connected to a cuff pressure controller 52, for instance by a pneumatic line 52A. In an embodiment, the cuff 51 is a dual-purpose tourniquet cuff that is inflated to control blood flow past the cuff 51. The cuff 51 may also sense a variation in blood penetration or blood flow in the portion of the limb encircled by the cuff 51, as described below.

In an embodiment, the cuff 51 is a strap that can be attached around a limb, so as to surround the limb. The cuff 51 includes an inflatable bladder(s) having a length sufficient to surround the limb at a desired location proximal to the surgical site. The pneumatic line 52A, for instance flexible tubing, may be a continuous pneumatic passageway that pneumatically connects the inflatable bladder within the cuff 51 to the pressure controller 52.

The pressure controller 52 may be an assembly of components, for instance including hardware and software for instance hosted by the processor unit 15, for regulating the pressure of air or liquid fluid in the inflatable bladder of the cuff 51. The pressure controller 52 may include a combination of valves and a pressure source, such as a pump, compressor, or the like, for closely controlling the pressure level within the inflatable bladder of the cuff 51. The pressure controller 52 may further include sensors to monitor the pressure, and other modules such as a condition detector that monitors the operation of the hardware components of the pressure controller 52 through sensor signals indicative of operation conditions. The pressure controller 52 may further include a timer module producing an indication of the length of time the inflatable bladder of the cuff 51 has been inflated. The pressure controller 52 may produce such data, including surgical time, current pressure, target pressure, and other information such as pulse, pressure, blood flow, as described below. In an embodiment, the data is displayed on the interface 12 of the integrated robotic surgery system 10, for instance in split screen fashion, as shown 12C in FIG. 4.

Referring to FIG. 2, the tourniquet system 50 may further include a blood transducer 53 or like sensor. The blood transducer 53 may be in the form of a clip that attaches to a distal body portion, such as a toes of the patient in FIG. 2, i.e., distal to the cuff 51. The blood transducer 53 produces signals indicative of blood pressure.

One or more ultrasound probes 54 are secured to the cuff 51. In an embodiment, the ultrasound probes 54 include transducers that emit an ultrasound wave and measure the time it takes for the wave to echo off of body tissue, body fluids and return to the transducer face. Using the known speed of the ultrasound wave, the time measurement is translated into a distance measurement between the ultrasound probe 54 and the body features. The transducers in the probes 54 may be single-element or multi-element transducers. For example, the probes 54 may be high-frequency linear transducers. Other embodiments include the probes 54 having multiple elements arranged in a phased array, having the capacity of performing multi-element wave generation for sound wave direction control and signal reconstruction. In an embodiment, the ultrasound probes 54 have the capacity of performing Doppler ultrasonography, so as to assess the blood flow velocity and direction sampled over a period of time, with the capacity of obtaining an assessment in real-time or with limited delay.

The tourniquet system 50 has a tourniquet control module 55. The tourniquet control module 55 may be operated by the processor unit 15 to operate various components of the tourniquet system 50, such as the blood transducer 53 and the ultrasound probe(s) 54. The tourniquet control module 55 may work in conjunction with the cuff pressure controller 52 so as to automatically control the operating parameters of the cuff pressure controller 52, or as a function of manually entered parameters for the tourniquet control module 55. As part of the tourniquet control module 55, a blood flow monitoring submodule 55A receives the data from the probe(s) 54. The blood flow monitoring module 55A is configured to assess blood flow characteristics, such as blood flow, and blood flow velocity from the readings of the probe(s) 54. In an embodiment, the blood flow monitoring module 55A uses the Doppler effect, calculating the frequency shift of an artery or vein, to determine the blood flow velocity.

In a variant, the blood flow monitoring module 55A proceeds with image segmentation to fit a cross-sectional shape representative of the artery. The fitting of the cross-sectional shape enables the evaluation of the artery size. The image segmentation may or may not be assisted by the operator, for instance via a visual display of the artery from the ultrasound imaging, on the interface 12. Using the size, the blood flow monitoring module 55A may calculate blood flow, i.e., blood flow=(artery area)*(blood speed), to use blood flow as an alternative to speed to adjust tourniquet pressure. In an embodiment, the blood flow monitoring module 55A integrates values of blood flow over time to get a normalized blood flow value. The normalized blood flow value, or other values such as normalized velocity, nominal velocity, systolic velocity, as calculated by the blood flow monitoring module 55A, may be used to loop back to the tourniquet 51 to apply a pressure correction via the cuff pressure controller 52 in order to reduce or increase compression. In an embodiment, the blood flow characteristics are imaged on a color scale, for instance on the interface 12. In another embodiment, the waveform of blood flow velocity over time may be produced and output on the interface 12. In another embodiment, with the values from the blood flow monitoring module 55A, the cuff pressure controller 52 controls the pressure in the cuff 51 using a proportional loop or a PID loop.

Stated differently, the pressure in the cuff 51 is adjusted as a function of the commands from the cuff pressure controller 52 using data from the blood flow monitoring module 55A, based on a monitoring of the velocity decrease in the blood flow. For example, the pressure increase in the cuff 51 may be gradually be decelerated (i.e., reduced) when approaching a target blood flow condition or blood pressure. Consequently, the pressure in the cuff 51 may be prevented from being excessive, by the monitoring the impact of the tourniquet on the blood flow.

Still referring to FIG. 2, as part of the tourniquet control module 55, a blood pressure monitoring submodule 55B receives the data from the blood transducer 53. The blood transducer 53 employs photoplethysmography, and produces a signal indicative of arterial blood penetrating past the cuff 51. The blood pressure monitoring module 55B processes the signals from the blood transducer 53 to indicate blood penetration. The blood pressure monitoring module 55B may be configured to automatically determine the limb occlusion pressure (LOP) at a time prior to the commencement of surgery when blood penetration past the cuff 51 is permitted and will not interfere with the surgical operation. In an embodiment, the LOP is the minimum level of pressure required in the inflatable bladder of the cuff 51 to stop arterial blood from penetrating the limb past the cuff 51. The LOP or other blood pressure values may be used concurrently or redundantly to the blood flow velocity values from the blood flow monitoring module 55A, so as to ensure that the tourniquet pressure is suitable. Stated differently, the blood flow characteristics measure by the combination of the blood transducer 53 and blood pressure monitoring module 55B may be used to confirm the data provided by the blood flow monitoring module 55A, via the cuff 51 and transducers 54. Any discrepancy may result in a warning to a user, or to the decrease in cuff pressure, for the blood pressure monitoring to note a return to a suitable condition. For example, the blood flow velocity and/or the LOP may be associated to a recommended tourniquet pressure that will be applied by the cuff 51.

The tourniquet control module 55 may display a GUI for interface 12 to display information to the user and to permit the user to control the operation of the tourniquet system 50. For example, a user of the tourniquet system 50 may initiate or confirm desired actions to be performed by touching the interface 12. As examples, a user of the integrated robotic surgery system 10 may operate the cuff 51 and blood transducer 53 to determine the LOP, may operate the cuff 51 to maintain a level of pressure based on blood flow velocity, though this may be done automatically; adjust the level of pressure maintained in the cuff 51; initiate the inflating of the cuff 51; initiate the depressurization of the cuff 51; set a time limit for tourniquet action. A user may be selectively prevented from initiating some actions when hazard conditions are detected for instance via the values of the tourniquet control module 55. The tourniquet control module 55 may be preprogrammed with inflating/deflating sequences, in the form of specific time on time off, as a possibility.

Referring to FIG. 3, the tourniquet system 50 may therefore be programmed to control a tourniquet pressure by performing a method 58 that may include one or more of:

- 58A, inflating or deflating a cuff or like device, or tightening such a device around a limb (commonly, a tourniquet), so as to control a tourniquet pressure. The tourniquet pressure may not necessarily be a pneumatic inflating/deflating, as it may be a tightening of a strap-like device, or the like.
- 58B, calibrating an ultrasound probe(s) to image blood flow characteristics at or downstream of the tourniquet, so as to image the impact of the tourniquet on the blood flow of the limb. The calibrating may include adjusting parameters of operation of the ultrasound probe(s) to obtain ultrasound signals representative of blood flow in an artery. The calibrating may be performed in an automated fashion.
- 58C, obtaining ultrasound readings indicative of the blood flow in the limb, with the tourniquet applying pressure on the limb. Obtaining the ultrasound readings may be continuous, and may occur when the tourniquet is applying pressure. Obtaining the ultrasound readings may also be periodic, for instance at fixed intervals. The intervals may vary according to the blood flow characteristic, tourniquet pressure, or the like, for instance with smaller intervals in proximity to the LOP. The readings may also switch to a continuous mode in proximity to the LOP or other target pressure or blood flow characteristic.
- 58D, determining at least one characteristic of the blood flow from the ultrasound readings of 58C. The at least one characteristic may be the volumetric blood flow, the blood flow velocity, etc.
- 58E, adjusting a tourniquet pressure as a function of the at least one characteristic of the blood flow. The adjusting may include inflating or deflating a bladder within the cuff 51 in an embodiment.

The method 58 may further include: using the ultrasound data to track a position and/or orientation of the limb in a referential coordinate system; monitoring the blood pressure distally to the tourniquet, and adjusting the tourniquet pressure in 58E as a function of the blood pressure; performing any of the steps automatically; decelerating a variation of tourniquet pressure as the blood flow characteristic approaches a target.

These features of the tourniquet system 50 and other features may be present, for instance as described in U.S. Pat. Nos. 7,771,453; 9,113,895; 9,039,730, 7,758,607; 8,480,842; 8,137,378; 7,780,698; 8,142,472; 8,425,551; 9,011,483; all of which are incorporated herein by reference.

In an embodiment, the tourniquet cuff 51 and ultrasound probe(s) 54 are also used in order to track bones in a referential coordinate system of the robot arm 20 (if present), or in other applications of computer-assisted surgery. A set of two or more probes 54 may be used to determine the anatomical axis. With the cuff 51 surrounding the limb of the patient, probes 54 are on various points of view of the bone. The anatomical axis of the bone is determined by locating the midpoint between two or more probes 54 and forming a line from these points along the bone. Moreover, the readings from the probes 54 may be used to perform a 3D image reconstruction of the bone, by the processor 12 of the CAS tracking system.

The position of the cuff 51 in space may then be determined using a reference marker 16. Therefore, in an embodiment, one or more ultrasound probes 54 are used to determine the anatomical axis of a limb, if the reading from the ultrasound probe(s) 54 provides a position from which more than one point on a line can be determined. A spatial correction may be effect using available imaging information, from partial 2d to 3D data, from pre-operative imaging to self-mapping. The spatial correction may be in 6 degrees of freedom.

Referring concurrently to FIGS. 1 and 2, a tracking camera is generally shown at 60. According to an embodiment, the tracking camera 60 uses retro-reflective markers 61A, 61B that are optically seen and recognized by the tracking camera 60 to track the robot arm 20 and/or the cuff(s) 51 on the limbs in six DOFs, namely in position and orientation. The camera 60 may have two points of view to determine the position and orientation of the markers 61A-B by triangulation, and peri-operative or intra-operative calibration or digitizing, image processing, etc, may be used to locate the bones and/or tools in the referential system X,Y,Z. An example of the camera technology is from Northern Digital Inc. The marker 61A is on the robot arm 20 such that its tracking allows the robot controller module 25 to calculate the position and/or orientation of the end effector 24. Likewise, marker 61B is on the cuff 51 such that its tracking allows the robot controller module 25 or other CAS system to calculate the position and/or orientation of the limb, using for instance the anatomical axis obtained from the tourniquet system 50 via the ultrasound readings. Other markers may be fixed directly to the patient bones, though such markers may be optionally. Bone markers attached to the patient need not be invasively anchored to the bone, as straps or like attachment means may provide sufficient grasping to prevent movement between the markers and the bones, in spite of being attached to soft tissue. However, the references could also be secured directly to the bones.

The markers can be provided in the form of retro-reflective markers or in the form of active emitters. In the illustrated embodiment, the markers 61A-B are retro-reflective markers. Accordingly, the camera 60 may illuminate the markers 61A-B during the surgery or using a reflection of ambient light on the markers 61A-B to observe the markers 61A-B. In an embodiment, the camera 60 may therefore be adapted to emit light which will be reflected by the retro-reflective markers 61A-B. For instance, if the markers 61A-B are passively reflecting markers, the camera 60 may have a light source chosen to exhibit a spectral profile to be transmitted through a filter. Alternatively, if the markers 61A-B are fluorescent markers, the light source of the camera 60 is selected to have a spectral profile suitable for generating fluorescence from the markers 61A-B, with a filter including a spectral pass band for transmitting the emitted fluorescence. One example of such markers includes passive infrared (IR) markers which are specifically designed to reflect light in the infrared portion of the electromagnetic spectrum, in which case the camera 60 may have an IR light source. As an alternative to optical tracking, the tracking system may consist of inertial sensors (e.g., accelerometers, gyroscopes, etc) that produce tracking data to be used by the robot controller module 25 to assist in continuously updating the position and/or orientation of the robot arm 20 bones. Other types of tracking technology may also be used. The use of the marker 61B may be used in conjunction with the ultrasound readings in order to track the bone. For example, tracking techniques combining optical tracking and ultrasound tracking may be used, as described in U.S. patent application Ser. No. 17/206,552, filed on Mar. 19, 2021 and incorporated herein by reference. The readings from the probes 54 may be used to perform a 3D image reconstruction of the bone, by the processor unit 15, and then identify a center of the bone segment, the anatomical axis passing through the center or being positioned relative to the center. This tracking may be performed by the processor unit 15 in a tracking module 65. The tracking module 65 may be tasked with performing the 3D image reconstruction of the bone from the ultrasound readings, and combining same with the tracking data from the camera 60, to track the bone for position and orientation. The tracking module 65 may obtain measured echo signals from the probes 54 and returning from the bone, to generate respective imaged echo datasets. With the coordinates of the probes 54 from the tracking system 60, the tracking module 65 may generate corresponding coordinate datasets, to then register the imaged echo datasets in a common coordinate system based on the coordinate datasets. Tracking of the position and orientation of the bone by the tracking module 65 with the registering. This may be done continuously, for example, and may be done concurrently with the determination of blood flow characteristics, as described herein. Stated differently, the tracking module 65 may obtain ultrasound readings representative of a bone of the limb; identify and track an axis of the bone from the ultrasound readings representative of the bone; and combine the axis of the bone to an optical tracking of the tourniquet to track the bone for position and orientation concurrently with the adjusting of the tourniquet pressure.

Referring to FIG. 1, the integrated robotic surgery system 10 may include a robot sterilization unit 70 in accordance with some embodiments. The robot sterilization unit 70 may operate jointly with the robot arm 20. The sterilization unit 70 may be embedded in the casing 11 of the integrated robotic surgery system 10.

The sterilization unit 70 may include a receptacle in the casing 11, for instance accompanied with a tray, that may be used to output an instrument. In yet another example, a door of the sterilization unit 70 may open to allow a user to remote an instrument. In still another example, the robotic arm 20 may be used to retrieve an instrument from within the sterilization unit 70. For example, the robotic arm 20 may retrieve an instrument from within the sterilization unit 70 based on known locations of instruments within the sterilization unit 70.

A door may be used to reload the sterilization unit 70 in an example. The sterilization unit 70 may include a sterile environment without the capability of sterilizing instruments. In this example, the sterilization unit 70 is a passive sterile storage unit. In another example, the sterilization unit 70 may be used to sterilize an instrument. In this example, the sterilization unit 70 may use sterilization equipment to sterilize the instrument, such as by using ultraviolet light, steam, gas, an autoclave, alcohol, heat pressure, glass beads, or the like. By-products of the sterilization unit 70 such as excess steam or heat may be harvested by the integrated robotic system and the energy stored in batteries for use in powering the various subsystems.

The sterilization unit 70 may be controlled by the user interface 12 or control mechanism, such as one incorporated in the casing 11 or one also used to control the robotic arm 20 (e.g., an augmented reality user interface, a display screen, a microphone and algorithm for interpreting audible commands, the robotic arm 20 itself, or the like). Controls may include initiating sterilization of an instrument (or all instruments within the sterilization unit 70) or outputting an instrument (e.g., opening a door, outputting a specific selected instrument, outputting a next instrument in a procedure, or outputting a machine learning model identified instrument at a particular step in a procedure).

The instrument may be output automatically, for example based on surgeon preferences, a machine learned model, or the like. For example, image processing may be used to determine a step of a procedure that is completed or almost completed, and an instrument for a next step may be output. In another example, movement of the robotic arm 20 may be used to determine that an instrument is needed and output that instrument. In this example, the movement may be a stored movement or a movement unique to a portion of a surgical procedure that identifies a next step.

Referring to FIG. 4, a display of the interface 12 is shown, with the zones 12A, 12B, 12C respectively occupied by the GUIs of the robot arm 20, of the fluid waste management system 30 and of the tourniquet system 50. While these systems could have their own touchscreen, the combination of these systems into a single control panel may facilitate their use, and may reduce the number of parts within the operating room. It is contemplated to have other interfaces available in synchronicity with the interface 12, such that various operators could perform control commands from various locations. For example, a duplication of a given GUI could be displayed on a handheld device in closer proximity to the surgical site, for instance to give closer access to a surgeon. Thus, the zones 12A, 12B and/or 12C may be displayed contemporaneously. A zone could be hidden when a subsystem associated with the zone is not being used. Additional GUIs may be provided in a zone, such as for the debridement subsystem.

The integrated robotic surgery system 10 may therefore be generally described as including at least the casing 11, one or more processor units 15, the robotic arm 20 mounted to the casing 11, the fluid waste management subsystem 30 having the one or more reservoirs 33, and the vacuum pump 31 in the casing 11. The robotic controller module 25 and the waste management module 35 may be operated by the processor unit 15. The interface 12 having a display screen, the display screen producing graphic-user interfaces from both the robotic controller module 25 and the waste management module 35.

EXAMPLES

The following examples can each stand on their own, or can be combined in different permutations, combinations, with one or more of other examples.

Example 1 is an integrated robotic surgery system comprising: a casing; at least one processor unit; a robotic arm mounted to the casing; a fluid waste management subsystem having at least one reservoir, and a vacuum pump in the casing; a robotic controller module and a waste management module operated by the processor unit; and an interface having a display screen, the display screen producing graphic-user interfaces associated with both the robotic controller module and the waste management module.

In Example 2, the subject matter of Example 1 includes, wherein the casing is on casters.

In Example 3, the subject matter of Example 1 includes, wherein a footprint of the casing is at most 8.0 ft$^2$.

In Example 4, the subject matter of Example 1 includes a debridement subsystem, a debridement module operated by the processor unit; and a graphic-user interface associated with the debridement module.

In Example 5, the subject matter of Example 4 includes, wherein the debridement subsystem includes at least one nozzle operatively connected to the casing for feeding a debridement fluid to the at least one nozzle.

In Example 6, the subject matter of Example 1 includes a tourniquet subsystem, a tourniquet control module operated by the processor unit; and a graphic-user interface associated with the tourniquet control module.

In Example 7, the subject matter of Example 1 includes, further including a power module in the casing.

In Example 8, the subject matter of Example 1 includes, wherein the display screen is mounted to the casing.

In Example 9, the subject matter of Example 1 includes, wherein at least two of the graphic-user interfaces are displayed contemporaneously on the interface.

The invention claimed is:

1. A system for controlling a tourniquet pressure, comprising:
   a processing unit; and
   a non-transitory computer-readable memory communicatively coupled to the processing unit and comprising computer-readable program instructions executable by the processing unit for:
      obtaining ultrasound readings indicative of a blood flow in a limb having a tourniquet applying pressure on the limb;
      determining at least one characteristic of the blood flow from the ultrasound readings;
      obtaining signals indicative of a blood pressure downstream of a cuff of the tourniquet; and
      adjusting a tourniquet pressure as a function of the at least one characteristic of the blood flow and of the blood pressure downstream of the cuff of the tourniquet.

2. The system according to claim 1, wherein obtaining the ultrasound readings includes operating a phased array of probes in Doppler ultrasonography.

3. The system according to claim 1, wherein determining the at least one characteristic of the blood flow includes determining one or more of a volumetric blood flow, a blood flow velocity, a normalized velocity, a nominal velocity, and a systolic velocity.

4. The system according to claim 1, wherein obtaining the signals indicative of the blood pressure includes using photoplethysmography.

5. The system according to claim 1, including comparing the blood pressure with the at least one characteristic of the blood flow.

6. The system according to claim 5, wherein adjusting the tourniquet pressure includes reducing the tourniquet pressure or reducing a pressure increase for the tourniquet pressure when determining a discrepancy in the comparing.

7. The system according to claim 1, including determining a limb occlusion pressure with the signals indicative of the blood pressure and the tourniquet pressure.

8. The system according to claim 7, wherein adjusting the tourniquet pressure includes controlling the tourniquet pressure for the blood pressure to be above the limb occlusion pressure to maintain blood flow in a limb.

9. The system according to claim 7, wherein adjusting the tourniquet pressure includes reducing an increase in the tourniquet pressure as the blood pressure approaches the limb occlusion pressure.

10. The system according to claim 1, wherein obtaining the ultrasound readings occurs continuously at least during a period of controlling the tourniquet pressure.

11. The system according to claim 1, further including automatically releasing the tourniquet pressure after a fixed time period of maintaining the tourniquet pressure above a given threshold.

12. The system according to claim 1, further including automatically releasing the tourniquet pressure after a fixed time period of applying the tourniquet pressure.

13. The system according to claim 1, further adjusting the tourniquet pressure includes operating preprogrammed sequences of increasing and decreasing the tourniquet pressure.

14. The system according to claim 1, wherein adjusting the tourniquet pressure includes adjusting the tourniquet pressure in a proportional loop or a PID loop.

15. The system according to claim 1, wherein determining the at least one characteristic of the blood flow from the ultrasound readings includes performing image segmentation to fit a cross-sectional shape representative of an artery of the limb.

16. The system according to claim 1, wherein adjusting the tourniquet pressure includes inflating and deflating a cuff of a tourniquet system.

17. The system according to claim 1, further including obtaining ultrasound readings representative of a bone of the limb.

18. The system according to claim 17, further including identifying and tracking an axis of the bone from the ultrasound readings representative of the bone.

19. The system according to claim 18, further including combining the axis of the bone to an optical tracking of the tourniquet to track the bone for position and orientation concurrently with the adjusting of the tourniquet pressure.

20. The system according to claim 1, wherein obtaining the ultrasound readings includes obtaining the ultrasound readings from at least one probe on the tourniquet.

* * * * *